United States Patent [19]

Takayama

[11] 4,329,629

[45] May 11, 1982

[54] LIGHT SOURCE UNIT HAVING A NUMBER OF FLASH TUBES

[75] Inventor: Syuichi Takayama, Hachioji, Japan

[73] Assignee: Olympus Optical Co., Ltd., Tokyo, Japan

[21] Appl. No.: 122,175

[22] Filed: Feb. 19, 1980

[30] Foreign Application Priority Data

Mar. 2, 1979 [JP] Japan .................. 54-24146

[51] Int. Cl.³ .............. A61B 1/06; H05B 41/34
[52] U.S. Cl. ............................ 315/323; 128/6; 315/324; 350/174; 362/11
[58] Field of Search .......... 315/232, 240, 241 P, 315/313, 320, 323, 324; 354/62, 63; 350/171, 174, 285; 362/11, 15; 128/6-9

[56] References Cited

U.S. PATENT DOCUMENTS

| | | | |
|---|---|---|---|
| 3,694,696 | 9/1972 | Laskowski | 315/241 P |
| 3,864,600 | 2/1975 | Schneider | 315/241 P |
| 3,864,601 | 2/1975 | Schneider | 315/241 P |
| 3,924,937 | 12/1975 | Munroe et al. | 350/285 |

FOREIGN PATENT DOCUMENTS

| | | |
|---|---|---|
| 1184450 | 12/1964 | Fed. Rep. of Germany . |
| 2014662 | 10/1971 | Fed. Rep. of Germany . |
| 7808292 | 8/1972 | Fed. Rep. of Germany . |
| 2550891 | 5/1976 | Fed. Rep. of Germany . |
| 52-32320 | 3/1977 | Japan ................. 354/62 |

*Primary Examiner*—Eugene R. LaRoche
*Attorney, Agent, or Firm*—Frishauf, Holtz, Goodman and Woodward

[57] ABSTRACT

A light source unit for an endoscope is provided with a number of flash tubes which are caused in turn to emit a light. On an optical path passing through a light-incident surface of a light guide of the endoscope there are arranged, in corresponding relationship to the flash tubes, a number of plane reflecting mirrors which reflect the lights from the flash tubes toward the light-incident surface of the light guide, respectively. The reflecting mirrors are each movable, for example, by a rotary solenoid. This solenoid operates at the time when the light emission from one of the flash tubes is completed. Thus, the solenoid, for the purpose of giving the optical path for a succeeding one of the flash tube, removes from that optical path the reflecting mirror corresponding to said one of the flash discharge tubes.

11 Claims, 16 Drawing Figures

F I G. 4A
LIGHT INTENSITY
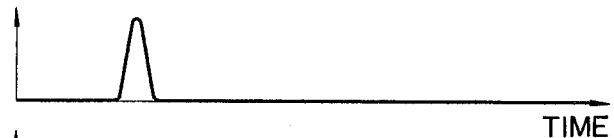
TIME
F I G. 4B
LIGHT INTENSITY
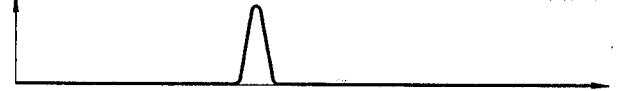
TIME
F I G. 4C
LIGHT INTENSITY
TIME
F I G. 4D
LIGHT INTENSITY
TIME
F I G. 4E
VOLTAGE
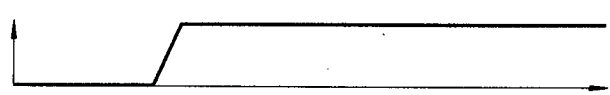
F I G. 4F
VOLTAGE
F I G. 4G
VOLTAGE
F I G. 4H
TRIGGERING PULSE
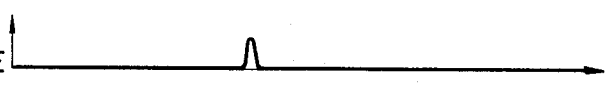
F I G. 4I
TRIGGERING PULSE
F I G. 4J
TRIGGERING PULSE
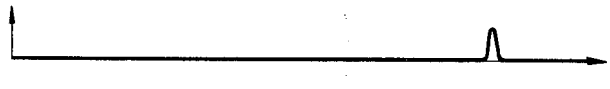
F I G. 4K
LIGHT INTENSITY

4,329,629

LIGHT SOURCE UNIT HAVING A NUMBER OF FLASH TUBES

BACKGROUND OF THE INVENTION

This invention relates to a light source unit having a number of flash tubes and, more particularly, to a high brightness light source unit for use in a photographing apparatus using an endoscope.

Generally, it is impossible to make a light guide for an endoscope large in diameter since part of it is required to be inserted into a human body and yet the light entering a light-incident surface of it is limited to one having an angle of incidence which falls within a specified range. It is difficult, therefore, to guide all light generated from one flash tube into the light guide. Conventionally, therefore, it was only possible to guide part of such light into the light guide. In the photographing which is effected using such a light guide, therefore, it was impossible to obtain a sufficient amount of light and so shortage of exposure was very likely to occur.

Accordingly, the object of the invention is to provide a light source unit for the photographing performed with the use of an endoscope, which unit is capable of introducing a sufficient amount of light into a light guide of the endoscope.

SUMMARY OF THE INVENTION

According to the invention, there is provided a light source unit comprising:

(a) a number of flash tubes caused in turn to emit a light;

(b) light reflecting means provided correspondingly to said flash tubes and arranged on the same optical path to reflect light emitted from the corresponding flash tubes in the same direction, and (c) moving means for removing the light reflecting means from the optical path when the light emission from the corresponding flash tube to the light reflecting means is completed, the optical path for a succeeding one of the flash tube being thus ensured.

BRIEF DESCRIPTION OF THE DRAWING

FIG. 4(A) to FIG. 4(D) are views showing light intensity waveforms of the flash tubes respectively FIG. 4(E) to FIG. 4(G) are views showing input voltage waveforms supplied to rotary solenoids respectively;

FIG. 4(H) to FIG. 4(J) are views showing triggering pulses applied to the flash tubes respectively;

FIG. 4(K) is a view showing a light intensity waveforms supplied to a light guide;

DETAILED DESCRIPTION

Figure 1:
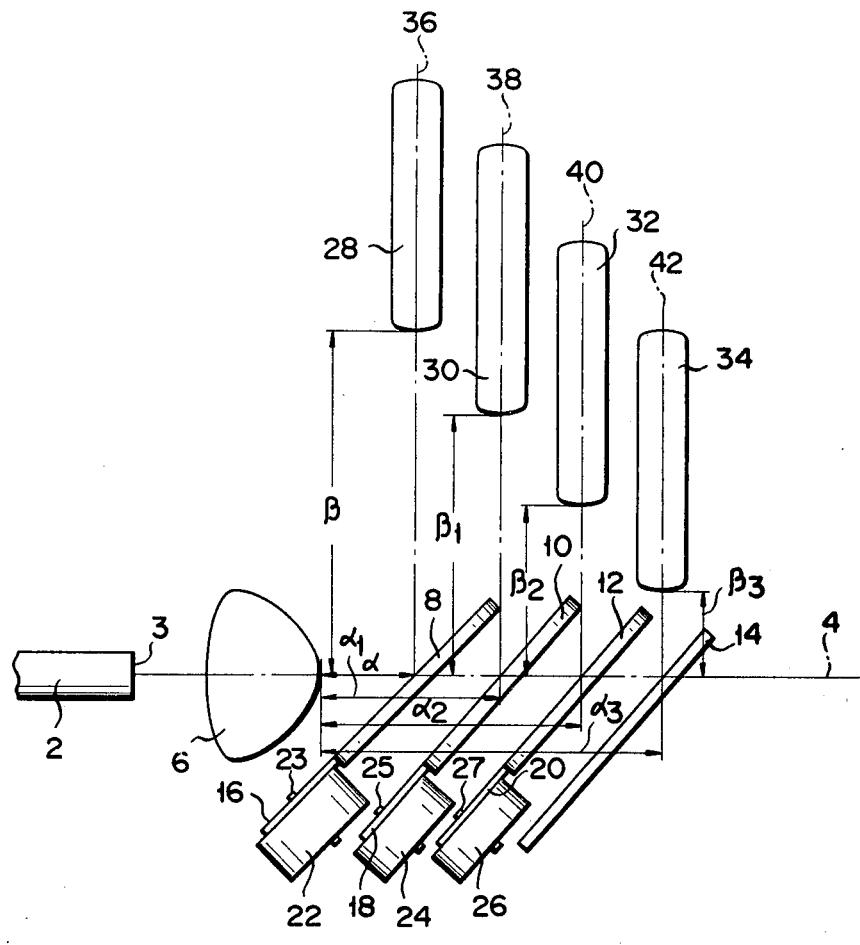
FIG. 1 is a side view schematically showing a light source unit equipped with a number of flash tubes according to an embodiment of the invention.

Referring to FIG. 1, an internal structure of a light source unit for an endoscope is schematically shown therein. A light guide 2 of the endoscope (not shown) is coupled to the light source unit and part of it extends into the light source unit. As well known, the light guide 2 extends into a portion of the endoscope which is to be inserted into a human body to reach a forward end of that endoscope portion. The light transmitted through the light guide 2 is irradiated onto a region to be photographed of the body cavity. The light reflected from such region is transmitted via an image guide into a camera unit. The light guide 2 has a light-incident surface 3. An optical axis 4 of the light-incident surface 3 extends forwardly, and at right angles to the light-incident surface. As well known, the light being introduced into the light guide 2 is limited to light rays having a specified angle of incidence taken with respect to the light-incident surface 3.

Along the optical axis 4 are arranged a focussing lens 6 and first, second, third and fourth plane reflecting mirrors 8, 10, 12 and 14 in that order. The focussing lens 6 is a lens for focussing the incident light onto the light-incident surface of the light guide 2. The focussing lens 6 focusses its incident light so that the light transmitted through it may define an angle of incidence, with respect to the light-incident surface of the light guide 2, which falls within a specified range as much as possible. The position of the focussing lens 6 is determined so that the lens 6 may be located at a specified distance from the light-incident surface of the light guide 2. The first, second and third plane reflecting mirror 8, 10 and 12 are inclined at a specified angle with respect to the optical axis 4 and are fixed at one end to supporting members 16, 18 and 20, respectively, which are respectively supported on rotating shafts 23, 25 and 27 of rotary solenoids 22, 24 and 26 in a manner that said members can be rotated about said rotating shafts. The fourth plane reflecting mirror 14 is fixedly disposed in a manner that it is inclined at a specified angle with respect to the optical axis 4. First, second, third and fourth flash tubes 28, 30, 32 and 34 are disposed, as shown, around the optical axis 4 in corresponding relationship to the first, second, third and fourth plane reflecting mirrors 8, 10, 12 and 14, respectively. In an example shown in FIG. 1, the first, second, third and fourth plane reflecting mirrors 8, 10, 12 and 14 are disposed so that each of their mirror surfaces may define an angle of 45° with respect to the optical axis 4. Optical axes 36, 38, 40 and 42 of the first, second, third and fourth flash tubes 28, 30, 32 and 34 are each arranged to define an angle of 45° with respect to a corresponding one of the plane reflecting mirrors 8, 10, 12 and 14, that is, to intersect the optical axis 4 at right angles thereto. When disposition and arrangement of the constituent elements are made as such, the lights which are emitted from the flash tubes 28, 30, 32 and 34 to advance along the optical axes 36, 38, 40 and 42 are reflected by the plane reflecting mirrors 8, 10, 12 and 14 and then advance along the optical axis 4. This means that the lights emitted from the flash tubes 28, 30, 32 and 34 are made incident upon the light guide 2. In the above-mentioned disposition of the constituent elements of the unit, the length of the paths of the lights emitted from the flash discharge tubes 28, 30, 32 and 34 are so substantially equalized as to permit equal amounts of light to enter the light guide 2. In other words, the length of optical path ($\alpha + \beta$), which is a sum of the distance as measured from the light-incident surface of the focussing lens 6 to a point of the first plane reflecting mirror 8 taken along the optical path 4 and the distance as measured from the mirror point to the lowest point of the tube 28 taken along the optical axis 36, is determined to become substantially equal to each of the optical path lengths $(\alpha_1+\beta_1)$, $(\alpha_2+\beta_2)$ and $(\alpha_3+\beta_3)$ where $\alpha_1$, $\beta_2$ and $_3$ represent the distances as measured respectively from the similarly taken points of the plane reflecting mirrors 10, 12 and 14 to the light-incident surface of the lens 6; and $\beta_1$, $\beta_2$ and $\beta_3$ the distances as measured respectively from such points of the plane reflecting mirrors 10, 12 and 14 to the similarly taken lowest points of the tubes 30, 32 and 34.

In the above-mentioned embodiment, reference was made to the case where the plane reflecting mirrors 8, 10, 12 and 14 each defined an angle of 45° with respect to the optical axis 4. The invention, however, is clearly not limited to such angle of 45°. Further, according to the invention, each plane reflecting mirror 8, 10, 12 or 14 may not be disposed at an equal angle with respect to the optical axis 4. Namely, each of the flash tubes 28, 30, 32 and 34 has only to be disposed at a position at which the light from it is to be regularly reflected from the corresponding plane reflecting mirror so as to permit that light to advance along and exactly in accord with the optical axis 4.

Figure 2:
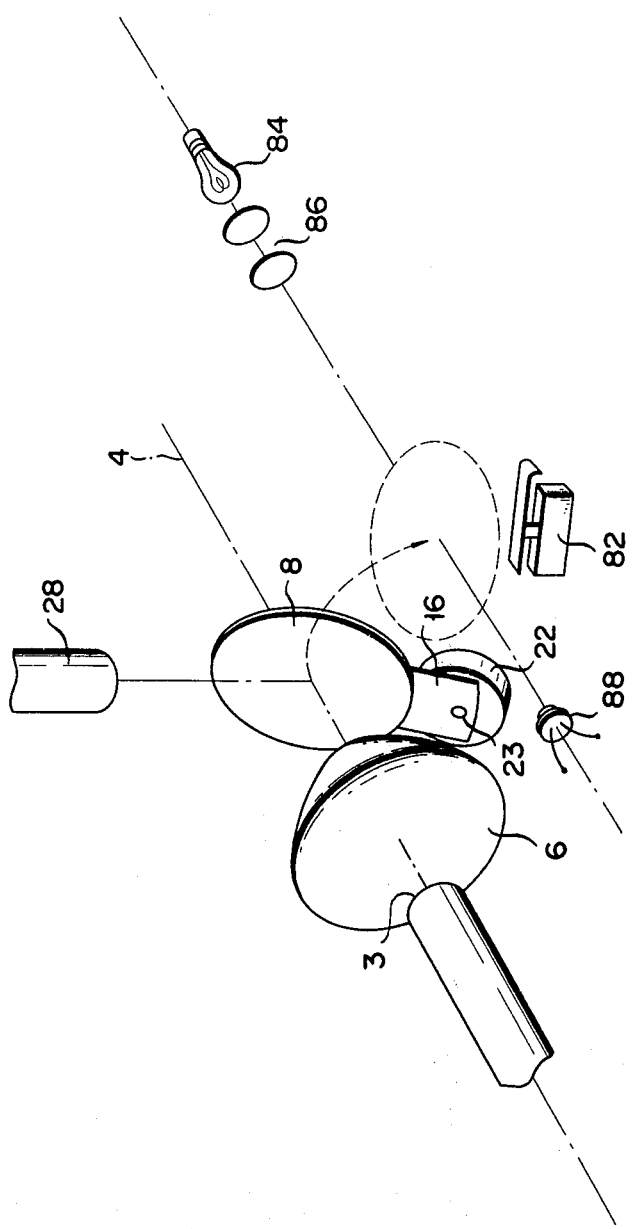
FIG. 2 is a perspective view for explaining the operation of the light source unit of FIG. 1 and a switch mechanism thereof.

With the above-mentioned construction, the first flash tube 28 is initially caused to emit a light. This light is reflected by the first plane reflecting mirror 8 and, after it has been focussed by the focussing lens 6, enters the light guide 2. Upon completion of the light emission from the first flash discharge tube 28, the first rotary solenoid 22 is energized and, as shown in FIG. 2, the first plane reflecting mirror 8 rotates, whereby this mirror is removed from the optical path of the mirrors 10, 12 and 14 situated behind the mirror 8. Upon removal of the first mirror 8, the second flash tube 30 is caused to emit a light, and then a similar operation is repeatedly carried out. For brevity of the description, in FIG. 2 the first plane reflecting mirror 8 is only shown. The second and third plane reflecting mirrors 10, 12 are sequentially caused to rotate in the same manner as the mirror 8. If the third plane reflecting mirror 12 is caused to rotate and the fourth flash discharge tube 34 is then caused to emit a light, it means a completion of the light emitting operation of the light source unit. If the respective amounts of lights emitted from the first, second, third and fourth flash discharge tubes 28, 30, 32 and 34 are equal, since the optical path lengths $(\alpha+\beta)$, $(\alpha_1+\beta_1)$, $(\alpha_2+\beta_2)$ and $(\alpha_3+\beta_3)$ as above measured from the flash tubes 28, 30, 32 and 34 to the light-incident surface of the focussing lens 6 are equal to each other, the substantially equal amounts of lights are successively allowed to enter one end of the light guide 2. As a result, a sufficient amount of light is irradiated from the other end of the light guide 2 onto a region to be photographed of the body cavity.

There will now be described an example of an electric circuit for causing the light source unit to make the above-mentioned operations by reference to FIG. 3.

Figure 3:
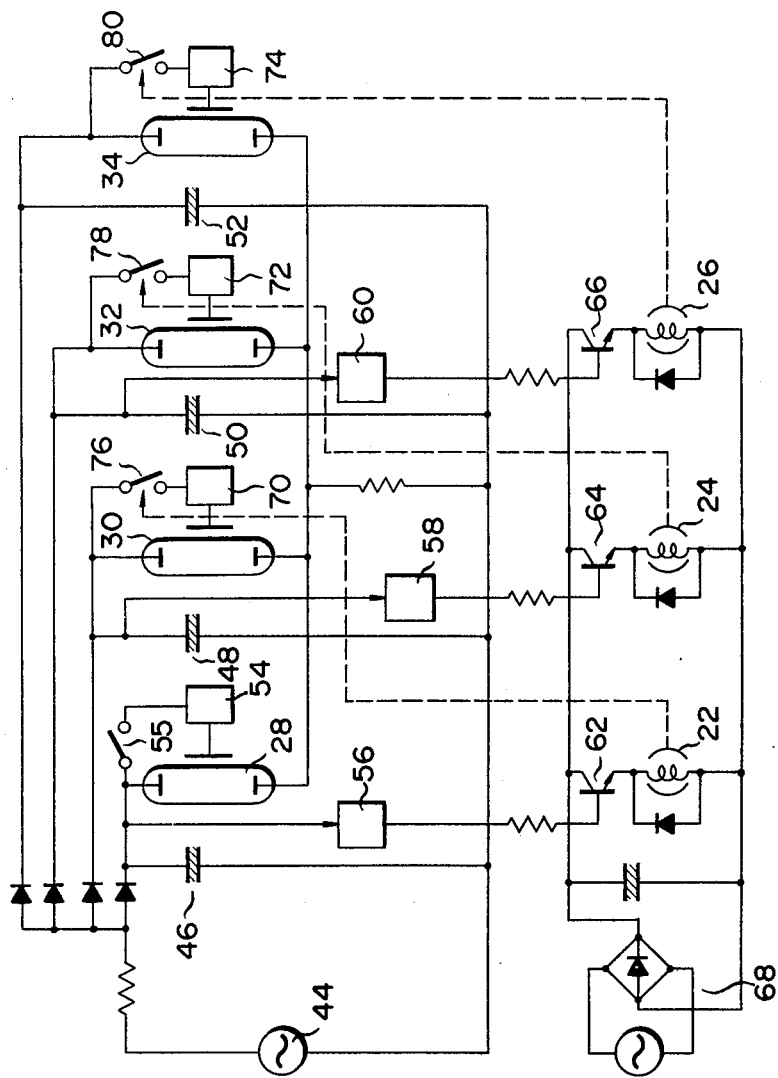
FIG. 3 is a circuit diagram showing an example of an electric circuit for the light source unit according to the invention.

Referring to FIG. 3, first, second, third and fourth main capacitors 46, 48, 50 and 52 are connected to a power source 44 through diodes, respectively. The above-mentioned flash tubes 28, 30, 32 and 34 are connected in parallel to said first, second, third and fourth main discharge capacitors 46, 48, 50 and 52, respectively. To a trigger electrode of the first flash tube 28 is connected a first trigger circuit 54, which is connected to the power source 44 through a trigger switch 55. This switch may be a synchronous contact of the camera. To the positive sides of the first, second and third main capacitors 46, 48 and 50 are connected voltage-level detecting circuits 56, 58 and 60 for detecting the voltage of those capacitors, respectively, which circuits 56, 58 and 60 are connected to bases of solenoid-driving transistors 62, 64 and 66, respectively, through resistors. The above-mentioned first, second and third rotary solenoids 22, 24 and 26 are connected to a power source 68 through collectors and emitters of the transistors 62, 64 and 66, respectively. To trigger electrodes of the second, third and fourth flash tubes 30, 32 and 34 are connected, as in the case of the first flash discharge tube 28, second, third and fourth trigger circuits 70, 72 and 74, respectively. The second trigger circuit 70 is connected to the power source 44 through a switch 76 arranged to be closed upon completion of the operation of the first rotary solenoid 22. The third and fourth trigger circuits 72 and 74 are connected to the power supply 44 through switches 78 and 80 arranged to be closed in corresponding relation to the operations of the second and third rotary solenoids 24 and 26, respectively. Each of the switches 76, 78 and 80 may for example be such a microswitch 82 being closed upon abutment of the mirror 8 against it as shown in FIG. 2, or may be such a combination of a lamp 84, focusing lens 86 and photo-transistor 88 as shown in FIG. 2. In such combination, the lamp 84, focussing lens 86 and photo-transistor 88 are disposed, as shown, so that, when the rotary solenoid 22 operates to cause the mirror 8 to rotate, the light emitted from the lamp 84 may be focussed by the focussing lens 86 thus to be prevented from going toward the photo-transistor 88. Thus, when the photo-transistor 88 becomes nonconductive, the trigger circuits 70, 72 or 74 are energized.

In the above-mentioned electric circuit, when the trigger switch 55 is closed, the first trigger circuit 54 is allowed to operate to supply a trigger voltage to the trigger electrode of the flash tube 28, thereby to cause the flash tube 28 to emit a light as shown in FIG. 4(A). When the light emission from the flash discharge tube 28 occurs, the voltage of the first capacitor 46 starts to drop. When this voltage reaches a specified value, the voltage-level detecting circuit 56 detecting this voltage and supplies a solenoid energizing signal to the base of the transistor 62. As a result, the transistor 62 is turned on and the first rotary solenoid 22 is energized as shown in FIG. 4(E), whereby the first mirror 8 is allowed to rotate. Upon rotation of this plane reflecting mirror 8, the switch 76 is closed to cause the second trigger circuit 70 to produce such a trigger voltage signal as shown in FIG. 4(H). As a result, the flash tube 30 starts to be discharged as shown in FIG. 4(B). Thereafter, similarly, as shown in FIG. 4(F) the second rotary solenoid 24 is energized, whereby the second plane reflecting mirror 10 rotates. As a result, the third trigger circuit 72 produces a trigger pulse voltage as shown in FIG. 4(I), whereby the third flash tube 32 is discharged as shown in FIG. 4(C) further, as shown in FIG. 4(G) the third rotary solenoid 26 is energized, whereby the third mirror 12 rotates. As a result, the fourth trigger circuit 74 produces a trigger pulse voltage as shown in FIG. 4(J), whereby the fourth flash tube 34 is discharged as shown in FIG. 4(D). As a result, such a flash light as shown in FIG. 4(K) is irradiated from said other end of the light guide 2.

The above-mentioned example of the electric circuit is arranged to operate so that the operation of the first plane reflecting mirror 8 and the flash tube 28 may be followed by the operation of the other plane reflecting mirrors and flash discharge tubes. According to the invention, however, the circuit may be arranged so that the operating time of every constituent element thereof may in advance be determined and, when the timer is turned on, the flash tubes and plane reflecting mirrors may be sequentially allowed to operate.

Figure 5:
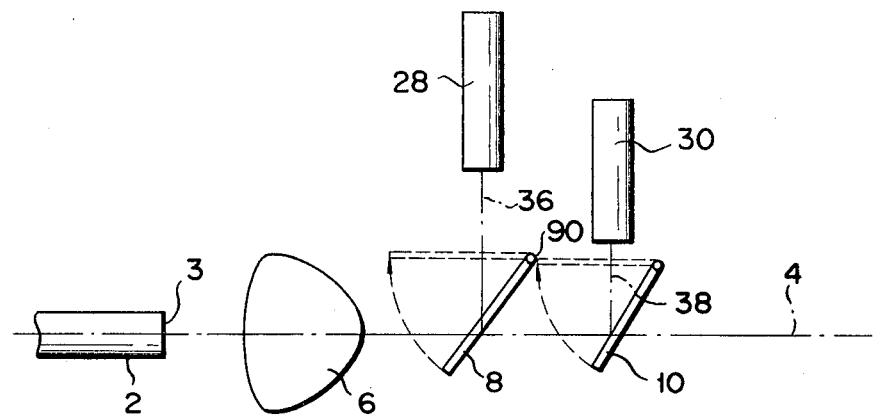
FIG. 5 is a side view schematically showing the light source unit according to another embodiment of the invention.
Figure 6:
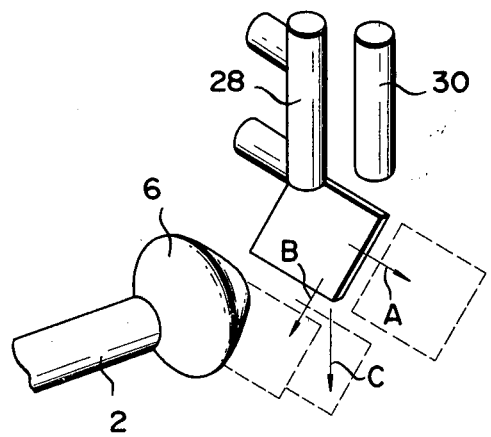
FIG. 6 is a perspective view schematically showing the light source unit according to still another embodiment of the invention.

FIGS. 5 and 6 show the light source units according to other embodiments of the invention. In the embodiment of FIG. 5, the plane reflecting mirror 8 is pivotally supported on a shaft 90 so as to rotate about the same toward the flash discharge tube 28. Namely, the mirror 8, upon completion of high emission by the flash tube 28, rotates as indicated in broken lines in FIG. 5. As a result, there is produced a light path for the plane reflecting mirror 10 situated behind the above rotated mirror 8 to reflect the light emitted from the flash discharge tube 30. In the embodiment shown in FIG. 6, the mirror 8 is laterally allowed to a slide in a direction indicated by an arrow A, or allowed to slide along a plane including the mirror 8 as indicated by an arrow B, or moved downwards or upwards (not shown) parallel as it stands as indicated by an arrow C. In this way, according to the invention, the movement of the reflecting mirrors is not subjected to any specific limitation, but such mirrors have only to be so moved as to go away from the optical axis 4.

In the above-mentioned embodiments, description was made of four combinations at maximum of the reflecting mirror and flash tube. But, the invention is not limited to such four combinations or less. If a combined set of linearly reflecting mirror and flash discharge tube is used at least two in number, it would well serve the purpose. Further, three or more such combined sets can apparently be arranged as required. The above-mentioned embodiments referred to the use of plane reflecting mirrors as the light reflecting means. Such mirrors, however, may apparently be replaced by light reflecting means such as prisms which would be capable of directing lights to the same optical axis to permit them to advance along and in accord with it. Further, such mirror may be formed into a partially concaved shape as to have a light-focussing function.

In the above-mentioned embodiments, the device for moving the reflecting mirrors was the rotary solenoid. This solenoid may be replaced by a motor. Further, such mirrors serving as the light reflecting means may be moved by a compressed air operated moving device.

As described above, according to the invention, since the light reflecting means such as the above-mentioned plane reflecting means is removed from the optical path as it becomes unnecessary and the flash tubes are not moved at all, it is possible to introduce into the light guide the light from the flash tube, with a sufficient accuracy. The timing for the light emission from the flash tube can easily be arranged to match with the timing for the removal of the light reflecting means from the optical path. Additionally, supply of a required amount of light into the light guide can be achieved very easily.

What is claimed is:

1. A light source unit for supplying light of a desired amount to a specified region, comprising:
    a number of electric flash tubes which are successively caused to emit light;
    a corresponding number of light reflecting members for reflecting the light beams from respective electric flash tubes and for supplying the light beams in a common optical path, said light reflecting members being pre-arranged in said common optical path in the order of light beam reception from said electric flash tubes; and
    moving means for successively removing said light reflecting members from said common optical path upon completion of light emission of the corresponding respective electric flash tube, thus ensuring the precise positioning of the optical path for the light beam from the next successive electric flash tube which is to be reflected by the next light reflecting member.

2. A light source unit according to claim 1, which is a light source for an endoscope having a light guide; and in which a light incident surface of said light guide of the endoscope is located at a position including said common optical path.

3. A light source unit according to claim 1 or claim 2, in which said light reflecting members are plane reflecting mirrors, and said mirrors are moved in parallel by said moving means.

4. A light source unit according to claim 1 or claim 2, in which said moving means includes switching means, said switching means being closed when a light reflecting member is removed by said moving means, which closure of said switching means causes energization of the next succeeding one of said electric flash tubes.

5. A light source unit according to claim 4 in which said light reflecting members are plane reflecting mirrors, and said mirrors are moved in parallel by said moving means.

6. A light source unit according to claim 1 or claim 2, in which the distance between said electric flash tube and the one of said light reflecting members corresponding thereto is so determined that all optical distances respectively as measured from a light-incident surface on said common optical path to said flash tubes via said light reflecting means may be equal to each other.

7. A light source unit according to claim 6
    in which said light reflecting members are plane reflecting mirrors, and said mirrors are moved in parallel by said moving means.

8. A light source unit according to claim 1 or claim 2, in which said moving means moves said light reflecting members in parallel to successively remove them from said common optical path.

9. A light source unit according to claim 1 or claim 2, in which said light reflecting members are plane reflecting mirrors.

10. A light source unit according to claim 1 or claim 2, in which said light reflecting members are pivotally mounted; and said moving means successively pivots said light reflecting members about their respective pivot points to successively remove said light reflecting members from said common optical path.

11. A light source unit according to claim 9, in which said light reflecting members are plane reflecting mirrors.

* * * * *